(12) United States Patent
Haase et al.

(10) Patent No.: US 8,981,155 B2
(45) Date of Patent: Mar. 17, 2015

(54) PROCESS FOR PREPARING AROMATIC AMINES

(75) Inventors: Stefanie Haase, Bretnig-Hauswalde (DE); Dusko Kadijevic, Dresden (DE); Anne-Kathrin Merten, Lauchhammer (DE); Michael Zoellinger, Eislingen (DE); Andreas Raichle, Ludwigshafen (DE); Alexander Schocker, Mannheim (DE); Sandra Mühlbeyer, Frankenthal (DE); Olaf Wiedenhoff, St. Leon-Rot (DE); Joana Coelho Tsou, Brüssels (BE)

(73) Assignee: BASF SE, Ludwigshafen (DE)

( * ) Notice: Subject to any disclaimer, the term of this patent is extended or adjusted under 35 U.S.C. 154(b) by 10 days.

(21) Appl. No.: 13/311,371

(22) Filed: Dec. 5, 2011

(65) Prior Publication Data

US 2012/0215029 A1 Aug. 23, 2012

Related U.S. Application Data

(60) Provisional application No. 61/419,907, filed on Dec. 6, 2010.

(51) Int. Cl.
| | | |
|---|---|---|
| *C07C 209/00* | (2006.01) | |
| *C07C 229/36* | (2006.01) | |
| *C07C 209/34* | (2006.01) | |
| *C07C 209/36* | (2006.01) | |
| *B01J 8/22* | (2006.01) | |
| *B01J 21/06* | (2006.01) | |
| *B01J 23/755* | (2006.01) | |

(Continued)

(52) U.S. Cl.
CPC .............. *C07C 229/36* (2013.01); *C07C 209/34* (2013.01); *C07C 209/36* (2013.01); *B01J 8/228* (2013.01); *B01J 2208/00132* (2013.01); *B01J 2208/00752* (2013.01); *B01J 2219/00202* (2013.01); *B01J 2219/00231* (2013.01); *B01J 2219/0024* (2013.01); *B01J 21/066* (2013.01); *B01J 23/755* (2013.01); *B01J 35/023* (2013.01); *B01J 37/0036* (2013.01)
USPC ......................................................... 564/420

(58) Field of Classification Search
None
See application file for complete search history.

(56) References Cited

U.S. PATENT DOCUMENTS

| | | | |
|---|---|---|---|
| 4,414,401 A | 11/1983 | Wintermeyer et al. | |
| 5,121,337 A | 6/1992 | Brown | |
| 5,856,577 A * | 1/1999 | Cordier et al. ................ | 564/412 |

(Continued)

FOREIGN PATENT DOCUMENTS

| | | |
|---|---|---|
| CA | 1211757 A1 | 9/1986 |
| DE | 2044657 A1 | 3/1972 |

(Continued)

OTHER PUBLICATIONS

International Search report—PCT/EP2011/071707 mailed Feb. 17, 2012.

*Primary Examiner* — Clinton Brooks
(74) *Attorney, Agent, or Firm* — Drinker Biddle & Reath LLP

(57) ABSTRACT

A process for preparing aromatic amines by hydrogenation of nitroaromatics in the presence of catalysts, forming a fluid, amine-comprising reaction mixture in a reactor, wherein chromatographic analysis of the reaction mixture is carried out to determine the concentration of nitro and nitroso compounds in the reaction mixture.

30 Claims, 9 Drawing Sheets

(51) Int. Cl.
*B01J 35/02* (2006.01)
*B01J 37/00* (2006.01)

(56) References Cited

U.S. PATENT DOCUMENTS

| | | |
|---|---|---|
| 6,350,911 B1 | 2/2002 | Sander et al. |
| 6,423,872 B2 | 7/2002 | Marion |
| 6,677,271 B1 | 1/2004 | Birke et al. |
| 6,680,280 B1 | 1/2004 | Birke et al. |
| 7,091,383 B2 * | 8/2006 | Vanoppen et al. ............ 564/422 |
| 7,595,424 B2 * | 9/2009 | Vanoppen et al. ............ 564/420 |
| 2004/0164247 A1 | 8/2004 | Riehle et al. |
| 2005/0119505 A1 | 6/2005 | Zehner et al. |
| 2005/0177003 A1 | 8/2005 | Vanoppen et al. |
| 2007/0149814 A1 | 6/2007 | van Laar et al. |
| 2008/0146848 A1 | 6/2008 | Vanoppen et al. |
| 2010/0130788 A1 | 5/2010 | Coelho Tsou et al. |
| 2011/0275858 A1 | 11/2011 | Coelho Tsou et al. |

FOREIGN PATENT DOCUMENTS

| | | |
|---|---|---|
| DE | 3040631 | 5/1982 |
| DE | 3245318 | 6/1984 |
| DE | 19857409 A1 | 6/2000 |
| EP | 0094876 A1 | 11/1983 |
| EP | 0124010 A1 | 11/1984 |
| EP | 1138665 | 10/2001 |
| EP | 1161297 A1 | 12/2001 |
| EP | 1165231 A1 | 1/2002 |
| EP | 1310302 | 5/2003 |
| EP | 1445246 A2 | 8/2004 |
| WO | WO-00/35852 A1 | 6/2000 |
| WO | WO-03/066571 A1 | 8/2003 |
| WO | WO-03/068724 A1 | 8/2003 |
| WO | WO-2005/037768 A1 | 4/2005 |
| WO | WO-2006/089906 A1 | 8/2006 |
| WO | WO-2008/138784 A1 | 11/2008 |
| WO | WO-2008/145179 A1 | 12/2008 |
| WO | WO-2010/076251 A1 | 7/2010 |
| WO | WO 2011/014481 | 11/2011 |

* cited by examiner

PROCESS FOR PREPARING AROMATIC AMINES

CROSS-REFERENCE TO RELATED APPLICATION

This application claims the benefit of U.S. Provisional Application Ser. No. 61/419,907 filed Dec. 6, 2010, the entire contents of which are incorporated herein by reference in its entirety.

FIELD OF THE INVENTION

The invention relates to a process for preparing aromatic amines by hydrogenation of nitroaromatics in the presence of catalysts.

The preparation of amines, in particular aromatic monoamines and/or polyamines, by catalytic hydrogenation of mononitro and/or polynitro compounds is known from the prior art.

BACKGROUND

DE-A 2 044 657 describes a process for preparing toluenediamine (TDA) by hydrogenation of dinitrotoluene (DNT) in the presence of nickel- or ruthenium-comprising hydrogenation catalysts.

EP-B1 1 138 665 describes a process for the catalytic hydrogenation of aromatic nitro compounds, in which the hydrogenation is carried out continuously using a catalyst comprising at least nickel and optionally aluminum. After carrying out the hydrogenation, the catalyst is separated from the reaction mixture in a separation zone.

The reaction mixture obtained when carrying out the hydrogenation of nitroaromatics in a reactor comprises not only the aromatic amines but also nitro and nitroso compounds which comprise, for example, the nitroaromatics used as starting materials or intermediates formed in the reactor. Nitro and nitroso compounds can decompose explosively, in particular on heating. For safety reasons, monitoring of the reaction mixture in respect of the concentration of nitro and nitroso compounds present therein is therefore important. The safety risk increases proportionately to the increase in the reactor size and to the reduction in the residence times in the reactor. It has to be ensured that these explosive compounds are reacted completely in the reactor before the reaction mixture is, for example, passed to a subsequent distillation.

A further problem encountered in the catalytic hydrogenation of nitroaromatics using nickel-comprising catalysts is that the catalysts are deactivated over time, with nitroaromatics accelerating the catalyst deactivation. The lower the activity of the catalyst, the smaller is the proportion of the starting materials converted into amines, so that the proportion of unreacted nitroaromatics remaining in the reactor increases and this in turn accelerates deactivation. Monitoring of the catalyst activity is therefore necessary, especially in order to introduce a sufficient amount of unexhausted catalyst into the reactor.

The monitoring of the concentration of nitroaromatics has hitherto been carried out either by UV/VIS methods after the catalyst has been separated off directly in the reaction mixture, in which case care has to be ensured that the detection limits achieved are significantly above the limit concentrations of nitroaromatics for catalyst deactivation, or by manual sampling, sample preparation and determination in the laboratory by polarographic or chromatographic methods. Disadvantages of manual sampling are the high personnel requirement and the risks arising from sampling. Owing to the time delay in the provision of analytical results, these manual methods are very disadvantageous for controlling the process.

In the case of such manual control, the aromatic amine/water mixture prepared can contain increased concentrations of nitroaromatics and these nitroaromatics can result in an appreciable irreversible reduction in the catalyst activity during relatively long periods of time. This can lead to complete cessation of the catalytic activity and thus to a stoppage of production.

These aromatic amines can be, for example, naphthalenediamines, xylylenediamines, toluenediamines, anilines and toluidines and also further aromatic amines and mixtures. The corresponding nitro compounds are dinitronaphthaienes, dinitroxylenes, dinitrotoluenes (DNT), aminonitrotoluenes (ANT), mononitrobenzene and mononitrotoluene.

The challenge faced by on-line determination of, for example, dinitrotoluene (DNT) in the matrix toluenediamine (TDA)/water with metallic catalyst is very great because of the high melting point of the sample of about 80° C. and the composition of the sample (many isomers), the solids content of metallic catalyst of from about 0.1 to 15% by weight and the need to measure DNT in the trace range of preferably from 3 to 30 ppm.

According to the prior art, the activity of the catalyst is followed by means of gas chromatography, for example by the method according to example 1 of WO 03/066571 A1.

WO 2006/089906 describes the determination of the concentration of nitro and nitroso compounds by means of UV/VIS spectroscopy. Here, separation of the catalyst from the reaction mixture is necessary. The detection limit of the determination is typically from 40 to 50 ppm.

The known methods are characterized by complicated handling and conditioning of samples, susceptibility to interference and a relatively high consumption of auxiliaries and utilities.

The continuous and fast monitoring and regulation of the actual concentration of nitroaromatics in the hydrogenation process is of particular importance for the preparation of aromatic amines.

The amines and diamines prepared are often processed further to produce isocyanates.

BRIEF SUMMARY

It is an object of the present invention to provide a process for preparing aromatic amines by hydrogenation of nitroaromatics in the presence of catalysts in a reactor, which allows simple on-line monitoring of the concentration of nitro and nitroso compounds in a reaction mixture comprised in the reactor.

The detection limit should be reduced compared to UV/VIS spectroscopy and the sensitivity should thus be increased.

A further object is to make possible pseudocontinuous or on-line monitoring of the catalyst activity in the reactor so as to detect a decrease in catalyst activity before the nitroaromatics concentration reaches a value at which it accelerates catalyst deactivation further and thus sets off a downward spiral. In the case of DNT, this means, for example, that DNT has to be detected in a concentration range below 30 ppm and preferably from 3 ppm to 30 ppm. A further object is to replace manual sampling and off-line analysis of nitroaromatics, since manual sampling represents a considerable safety risk and automation of the measurement can save a great deal of laboratory analysis and simultaneously provide the information more quickly for process control.

The object is achieved according to the invention by a process for preparing aromatic amines by hydrogenation of nitroaromatics in the presence of catalysts, forming a fluid, amine-comprising reaction mixture in a reactor, wherein chromatographic analysis of the reaction mixture or a measurement of the absorption of IR- and/or VIS-radiation through the reaction mixture is carried out to determine the concentration of nitro and nitroso compounds in the reaction mixture, with the result of the determination of the concentration of nitro and nitroso compounds being used for preferably automated process control or regulation of the hydrogenation.

BRIEF DESCRIPTION OF THE DRAWINGS

FIGS. 3-4 are chromatograms of the reaction mixture with the various isomers analyzed by method 3a.

DETAILED DESCRIPTION OF THE PREFERRED EMBODIMENTS

The process control or regulation of the hydrogenation preferably comprises a modification of the introduction of catalyst and/or nitroaromatics into the reactor.

To determine the concentration of the nitro and nitroso compounds, preference is given to producing and evaluating a gas chromatogram of the reaction mixture.

Determination of areas of the appropriate peaks in the chromatogram can be employed for determining the concentration of individual components of the reaction mixture.

The sample is preferably fed on-line via a bypass, preferably in automatically, to the chromatograph so as to give an accurate picture of the concentration conditions in the reactor very close to real time.

Figure 8:
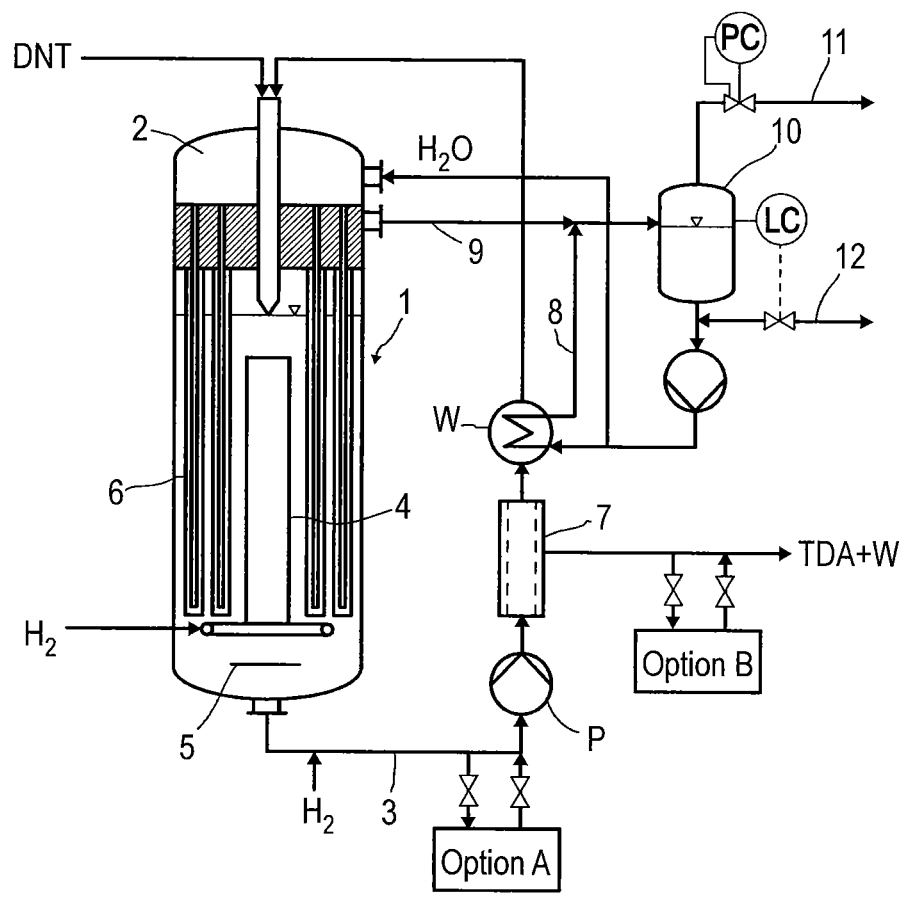
FIG. 8 schematically shows a plant for carrying out the process of the invention.

"On-line" sampling for chromatographic analysis means that sampling is carried out in a bypass for the liquid product output between reactor (e.g. stirred vessel, looped reactor, etc.) and product isolation unit (e.g. membrane filter, gravity separator, etc.), preferably by means of an additional (membrane) filter (option A) or in a bypass for the liquid product output downstream of the product isolation unit (e.g. membrane filter) (option B) (see FIG. 8).

Option A can preferably be equipped with a particle filter and a downstream automated liquid metering valve for sampling. As a result of sampling from the liquid product output between reactor and product isolation unit, the measurement is preferably carried out at a location at which the DNT concentration is low, i.e. typically via a catalyst separation unit distant from the introduction of DNT. As a result of sampling from the liquid product output, final monitoring of the mixing and reaction processes in the preceding reactors occurs at the same time. Measurements of the DNT concentration at various points directly in the reactor are technically much more complicated. The concentration ranges to be set would increase considerably with increasing proximity to the location at which DNT is introduced (and/or to regions of the reactor through which flow is poor). A disadvantage of this embodiment is the use of an additional unit for separating off the catalyst. Preferred embodiments of the additional unit for separating off the catalyst are ceramic membrane filters.

In option B, sampling for chromatographic analysis is carried out downstream of the product isolation unit. No additional catalyst separation unit is thus necessary for the measurement. A disadvantage is the worsening of the reaction time for regulating the hydrogenation since the sample is taken at a place further removed from the reactor. The metering of the reaction mixture into the gas chromatograph is preferably effected by means of an automatic liquid metering valve heated to at least 80° C.

The sample of the reaction mixture can be maintained at a temperature of at least 80° C. from sampling to analysis and optionally recirculation to the reaction mixture or be diluted with a solvent after sampling. This dilution is employed especially in the case of HPLC methods.

The object is additionally achieved by a method of regulating the concentration of nitro and nitroso compounds in a process for preparing aromatic amines by hydrogenation of nitroaromatics in the presence of catalysts, forming a fluid, amine-comprising reaction mixture in a reactor, which comprises the following steps:

a) recording of a chromatogram or IR- and/or VIS-spectrum or -absorption of the reaction mixture, b) input of the chromatogram recorded in step a) into a chromatogram evaluation unit (evaluation software) and/or into a chemometric calibration model or of the IR- and/or VIS-spectrum or IR- and/or VIS-absorption in a chemometric calibration model in order to determine the actual concentration of the nitro and nitroso compounds in the reaction mixture, c) determination of an intended-actual deviation of the concentration of nitro and nitroso compounds in the reaction mixture, d) regulation of one or more process parameters of the hydrogenation, on the basis of the intended/actual deviation determined in step c).

In step b), the chromatogram recorded can be input into a chemometric calibration model to determine the actual concentration of the nitro and nitroso compounds in the reaction mixture. Here, a simultaneous multicomponent analysis is carried out to achieve on-line quantification of the various reaction species (e.g. starting materials such as DNT and intermediates such as ANT) in the process. In order to be able to carry out the quantification, prior chemometric calibration of the analytical method is required. An overview of the use of multivariate chemometric calibration models in analytical chemistry is given in "Multivariate Kalibration", Jörg-Peter Conzen, 2001, ISBN 3-929431-13-0.

In step d), the introduction of catalyst and/or the introduction of nitroaromatics is preferably altered or regulated. In the case of a nitroaromatics concentration higher than the intended value, the introduction of catalyst is frequently increased and/or the introduction of nitroaromatics is reduced.

The object is also achieved by an apparatus for carrying out the above process for preparing aromatic amines, which comprises a reactor for the hydrogenation of nitroaromatics in the presence of catalysts, forming a reaction mixture, with a chromatograph for producing a chromatogram or a IR- and/or VIS-spectrometer for measuring the absorption of IR- and/or VIS-radiation through the reaction mixture to determine the concentration of nitro and nitroso compounds in the reaction mixture, where the apparatus is equipped to record chromatograms, with an evaluation unit for determining the concentration of nitroaromatics and a regulator unit for regulating the introduction of catalyst and/or introduction of nitroaromatics.

The apparatus preferably comprises:
a) means (202, 204) for recording a chromatogram of the reaction mixture,
b) a chromatogram evaluation unit (evaluation software) (206) and/or a chemometric calibration model (210) for evaluating the chromatogram to determine an actual concentration of nitro and nitroso compounds in the reaction mixture from the chromatogram,
c) means (212) for determining an intended-actual deviation,
d) means (212) for regulating one or more process parameters of the hydrogenation, in particular the introduction of the aromatic nitro compound (214) and/or introduction of the catalyst (216) on the basis of the intended/actual deviation.

In this context, nitro compounds are preferably aromatic compounds in which a hydrogen atom has been replaced by a nitro group ($NO_2$ group). Nitroso compounds are organic compounds which comprise the nitroso group (NO group) bound to an aromatic carbon atom. Amines are monoamines, diamines and polyamines. The fluid reaction mixture can be either liquid or gaseous.

According to the invention, the determination of the concentration of the nitro and nitroso compounds is carried out by quantitative evaluation of a (gas) chromatogram of the reaction mixture, generally by integration of the peak areas for the individual compounds to be analyzed.

The automatability of the operations in a chromatographic analysis and the short analysis times which can be achieved by application of modern chromatographic techniques allow continuous operation of the chromatograph (on-line in bypass) to be achieved. The results are made available for discrete times. The use of a fully automatically operating chromatograph leads to significant cost advantages compared to personnel-intensive laboratory analyses and gives, as a result of the pseudocontinuous provision of analytical values, a very detailed picture of the process in question A chromatographic process analysis facility comprises a device matched to the particular application for sampling, sample preparation and optionally switching of various sample streams, the actual analyzer and a device for processing and outputting the measured data.

In the modification of laboratory gas chromatographs for on-line analysis, the specific requirements for sample introduction and sample preparation, injection and data evaluation and management have to be taken into account. A graphical user interface "GC-Manager" is used for this purpose (GC-Manager is a registered trademark of BASF SE at the German Patent and Trademarks Office, Munich). The "GC-Manager" controls further (producer) programs remotely and thus ensures full functionality of the instrument and problem-free methods transfer. The data recording and processing is controlled by the "GC-Manager". The results of a GC analysis are automatically transmitted to data banks or user-defined MS Excel® tables. Furthermore, the "GC-Manager" also displays further important information such as the valve settings, the sample stream selected or the status of the analysis. A further feature of the software is communication with process control systems via analogue or digital interfaces. Direct transmission of the concentration values into the process control system and consequently regulation of the process are thus possible.

Both high performance liquid chromatography (HPLC) and technologies such as UPLC, UHPLC (ultra high performance liquid chromatography) derived therefrom and also gas chromatography are suitable for the analysis. Corresponding instruments for laboratory use and also for process measurements are commercially available (e.g. from Agilent Technologies (laboratory instruments) or Siemens AG (process instruments)). The advantage of chromatographic analysis is, in particular, that the various isomers of the starting material/materials, of the partially hydrogenated reaction products or the isomers of the fully hydrogenated reaction products can be detected, quantified and, by means of a subsequent mass-spectrometric detection, optionally also identified. Particular isomers can lead to undesirable secondary reactions which cause greater damage to the catalyst than others. The chromatographic analysis makes it possible to see whether the various isomers of the starting materials or intermediates react differently.

In a preferred embodiment of the invention, the content of nitroaromatics and nitrosoaromatics is determined on-line in the hydrogenation bath by means of a gas chromatograph (GC) during the hydrogenation. Here, the mixture to be analyzed having a melting point of about 80° C. is supplied in liquid form to the instrument, preferably automatically via a liquid metering valve, and then injected in liquid form. The supply of the sample in liquid form can be effected in two different ways:
1. dilution of the reaction mixture with a solvent (for example aniline in a ratio of from 1:4 to 1:1) and supply at, for example, room temperature;
2. continuous, nonstop heating of the feed and discharge lines for the reaction mixture to at least 80° C. so that the mixture remains liquid, as a result of which automated sampling is simplified.

Solidification of the reaction mixture interrupts the continuous supply to the chromatograph (analytical instrument), results in complicated cleaning and replacement of the line and interrupts the on-line analysis. In the preferred embodiment, the supply and metering is carried out according to option 2, in which a large amount of utilities (e.g. solvent aniline) can be dispensed with compared to option 1.

In the preferred reaction, the metering/injection of the sample conditioned by means of option 1 or option 2 into the gas chromatograph is carried out by means of an automated and heated liquid metering valve (Siemens AG). A small volume of the sample (about 0.6 µl) is vaporized and introduced in gaseous form into the separation column.

As regards the implementation in terms of instruments, laboratory or process instruments can be employed. An advantage of the use of a laboratory instrument is the ability of the present method to be applied quickly to on-line use in the process. In addition, in the case of a laboratory instrument, the speed of separation can be increased compared to a process instrument by means of programmed increase of the temperature in the column oven.

The results of the analysis (content of nitroaromatics and nitrosoaromatics determined from the corresponding peak areas in the chromatogram) are transmitted from the GC via typical process control interfaces to the process control system.

In the process of the invention, it is possible to carry out the measurements without the catalyst having been separated off beforehand. Owing to the solids content, in particular of relatively small catalyst particles (size<about 25 μm), it has been found that the measurements can be carried out more advantageously with prior removal of the catalyst. The reaction product is often discharged via a crossflow filter in a reactor having an external loop. The bypass is advantageously arranged downstream of the crossflow filter. This makes it possible for the chromatographic analysis to be carried out without further substantial sample preparation. For this purpose, a stream of the reaction mixture is branched off and conveyed to the (gas) chromatograph. This preferably happens on-line, i.e. in a bypass. It has found to be particularly advantageous to install an automated liquid metering valve in a bypass.

The concentration of the solid particles should preferably not exceed 15% by weight. Accordingly, it has been found to be particularly advantageous to install the GC measurement in a bypass and wherever possible equip it with suitable particle filters. In this way, the major part of the catalyst present can be separated off before carrying out the measurement, interferences in the measurements can be reliably avoided and cleaning and maintenance can be greatly reduced.

The method of separating off the catalyst can be selected from the group consisting of membrane filtration, sedimentation and centrifugation or the catalyst can be separated off using any other method known from the prior art. Methods of separating off a catalyst present in a reaction mixture are known, for example, from DE-A1 32 45 318, DE-A1 30 40 631 or WO 03/066571. It is also possible to use a combination of separation methods (for example sedimentation and subsequent membrane filtration) in order to achieve very complete removal of the catalyst from the reaction mixture before a chromatographic analysis is carried out.

In a preferred embodiment of the invention, the concentration is determined by evaluating the areas of the chromatogram recorded. The composition of the matrix is predetermined by the hydrogenation process and depends on the process parameters. The measured values are referenced to the results of laboratory studies (calibration curves).

This is carried out by GC measurements being carried out in the laboratory using synthetically produced samples having a known content of nitroaromatics and nitrosoaromatics and producing calibration curves.

This method enables even small amounts of nitroaromatics such as dinitrotoluene to be determined gas-chromatographically in the matrix in the concentration range 3-30 ppm in the product of hydrogenation processes.

To determine the concentration of the nitro and nitroso compounds, use is made of conventional (gas) chromatographs and separation columns, e.g. from Agilent Technologies (laboratory GC), from Restek (columns), from Siemens AG (process instruments).

The apparatus for IR and/or VIS measurements preferably comprises:
a) means (202, 204, 206, 208) for recording an infrared or VIS-spectrum of the reaction mixture,
b) a chemometric calibration model (210) for determining an actual concentration of nitro and nitroso compounds in the reaction mixture from the infrared spectrum,
c) means (212) for determining an actual/intended deviation,
d) means (212) for regulating one or more process parameters for hydrogenation, more particularly the metering of the aromatic nitro compound (214), based on the actual/intended deviation.

According to the invention, the concentration of the nitro and nitroso compounds is alternatively determined by measuring the absorption of infrared radiation in the reaction mixture. This can be near-infrared (NIR) radiation, mid-wavelength infrared radiation or Raman radiation. Work is preferably undertaken with NIR radiation. This measurement can be complemented or replaced by VIS measurements.

The concentration of nitro and nitroso compounds in the reaction mixture can be determined from a measured absorption of IR radiation by the reaction mixture. If monochromatic IR radiation with an initial intensity $I_0$ passes through a diluted solution of an absorbing substance (e.g. the reaction mixture) of thickness d, Lambert-Beer's law describes the absorption of the radiation by the solution. Lambert-Beer's law states that:

$$2.3 \cdot \log \frac{I_0}{I} = E = \varepsilon \cdot d \cdot c$$

where
$I_0$: Intensity of the radiation before entering the solution
I: Intensity of the radiation after passing through the layer thickness d
d: Layer thickness (e.g. cuvette dimensions) of the fluid (e.g. the solution) in cm
c: Concentration of the absorbing substance in mol/l
ε: Molar extinction coefficient in l/(mol×cm) (material constant)
E: Absorbance.

This results in a linear relationship between the concentration of the fluid and the absorbance. As a result, it is possible to determine the concentration of an absorbing sample by measuring the absorbance (for example using a spectrophotometer) by means of a calibration curve or a known extinction coefficient (photometry).

Removing the catalysts from the reaction mixture prior to determining the absorption can simplify the processing of the final product in the method according to the invention. Unlike UV/VIS spectroscopy, the reaction mixture need not be largely freed from black catalyst particles for measuring absorption because said particles have no substantial influence on the IR spectroscopy.

As a result, the method according to the invention allows the measurements to be carried out without previously removing the catalyst. This significantly reduces the requirements of the measurement instrumentation for preparing the sample. This affords the possibility of measuring the absorption of infrared radiation inline, without taking a sample. To this end, a flow of the reaction mixture is diverted and routed past a measurement cell for measuring the infrared radiation. This preferably happens online in a bypass. In the process, it was found to be particularly advantageous to install the infrared measurement probe in a bypass, which is equipped with, preferably automatic, valves in front of and behind the measurement probe. The valves can be closed for the measurement such that the catalyst contained in the reaction mixture can settle out. This affords the possibility of an even less noisy measurement of the IR absorption.

In order to determine the concentration of the nitro and nitroso compounds, it is possible to measure an absorption spectrum in a wavelength range of the IR radiation or the absorption (absorbance) of IR radiation can be measured at one wavelength. There preferably is a monochromatic measurement (using radiation at a selected wavelength). This is sufficient for determining the concentration of the nitro and nitroso compounds in the reaction mixture. The wavelength of the radiation is selected such that contributions of other components of the reaction mixture, more particularly the amines, to the absorption of the radiation are as low as possible.

In the case of an IR spectrum measurement, the measurement is preferably carried out in a wavelength range between 600 and 1365 nm, particularly preferably between 650 and 1200 nm. A monochromatic measurement preferably also lies at a wavelength in this wavelength range.

Measuring the absorption spectrum in a wavelength range belonging to IR radiation is advantageous in that incorrect measurements, which can for example be caused by gas bubbles in the reaction mixture, are easy to identify and are not used for determining the concentration. However, such a measurement of an absorption spectrum requires a more complicated photometer, in which both the light source contained therein and the detector must cover such a wavelength range.

According to a preferred embodiment of the present invention, there additionally is a measurement of the absorption of IR radiation by the reaction mixture in another wavelength range or at another wavelength for the purpose of baseline correction.

Such a baseline correction may be necessary for equalizing the influence of intensity variations of the light source emitting the IR radiation. For this purpose, the wavelength range or wavelength is selected such that the nitro and nitroso compounds make no or a negligibly small contribution to the measured absorption by the reaction mixture in this wavelength range or at this wavelength. This measurement provides a correction value. The concentrations of the nitro and nitroso compounds are determined in a wavelength range or at a wavelength in which/at which the nitro and nitroso compounds in the reaction mixture substantially absorb the IR radiation. The measured absorption is then corrected by the correction value, which was measured in the other wavelength range/at the other wavelength for the purpose of baseline correction. The absorption by the nitro and nitroso compounds and the correction values can simultaneously be measured continuously by means of two photometers set at different wavelength ranges. However, a spectrum comprising both wavelength ranges can also be recorded using one photometer or measurements can alternately be carried out at the two different wavelengths.

According to the present invention, the catalysts need not but can be removed from the reaction mixture using at least one removal method, which is selected from the group of membrane filtration, sedimentation and centrifugation or using any other method known from the prior art. By way of example, removing a catalyst contained in a reaction mixture is known from DE-A132 45 318, DE-A1 30 40 631 or WO 03/066571. A combination of removal methods is also possible (for example sedimentation and subsequent membrane filtration) in order to achieve very complete removal of the catalyst from the reaction mixture before absorption measurements are carried out.

According to the present invention, the IR radiation absorption can be measured at a pressure that is increased compared to ambient pressure and/or at ambient pressure. By way of example, a photometer can be arranged in a region behind a membrane filter for removing the catalyst, in which region the filtrate emerging from the filter is under increased pressure compared to the ambient pressure. However, the absorption measurement can also be arranged in a region of an apparatus for producing aromatic amines, in which the catalyst has already been removed and the reaction mixture has been depressurized to ambient pressure.

According to the invention, work is particularly preferably undertaken at a pressure to which the reaction mixture is subjected in the reactor. The reaction mixture out of the reactor under reaction pressure flows by way of the bypass. After closing the valves, the reaction mixture is likewise available at this pressure. A preceding separate removal of the catalyst is not required in this case since the sedimentation in the bypass after closing the valves is sufficient.

The absorption of IR radiation by the reaction mixture can be measured in the main flow taken out of the reactor or, preferably, in a bypass branching off from the main flow.

IR spectrometers, more particularly NIR spectrometers, that are suitable for the determination according to the invention are commercially available, for example from Bruker GmbH.

According to a preferred embodiment of the invention, the content of nitroaromatics and nitrosoaromatics during the hydrogenation are determined online in the hydrogenation bath by means of an NIR spectrometer and a calibration model, assisted by a suitable computer. The NIR spectrometer then transfers data, e.g. via a field bus, for outputting the content of nitroaromatics and nitrosoaromatics to the process control system. As a result of the determined content of nitroaromatics and nitrosoaromatics, regulation by the process control system is possible for the supply of a nitroaromatic.

In respect of the embodiment of the inline measurement of infrared spectra, preferably near-infrared spectra, and the evaluation of the measured spectra by means of a computer-assisted matrix-specific calibration model and the connection to a process control system, reference can be made to EP-A-1 445 246 for a more detailed description.

According to this method according to the invention, dinitrotoluene, more particularly 2,4-dinitrotoluene or the technical mixtures thereof with 2,6-dinitrotoluene, is preferably hydrogenated to the corresponding amine. According to a particularly preferred embodiment of the present invention, toluenediamine is produced by hydrogenating dinitrotoluene and the absorption of IR radiation is measured for substantially determining the concentration of dinitrotoluene and aminonitrotoluene contained in the reaction mixture. Aminonitrotoluene is an intermediate produced during the hydrogenation of dinitrotoluene. The measurement of the absorption, substantially by dinitrotoluene and aminonitrotoluene, in the reaction mixture is preferably carried out at a wavelength in the range between 600 and 1365 nm, preferably between 650 and 1200 nm, or an absorption spectrum is recorded over a wavelength range between 600 and 1365 nm. In the range between 665 and 965 nm, the radiation is substantially absorbed by the dinitrotoluene and aminonitrotoluene contained in the reaction mixture. The absorption by toluenediamine and the water contained in the reaction mixture is low in this wavelength range. Absorption measurements for the baseline correction can be carried out in a wavelength range between 650 and 750 nm, preferably at 700 nm. The absorption by dinitrotoluene and aminonitrotoluene is almost zero in this wavelength range.

The IR spectrometer contains an IR light source and a detector, with a container through which the reaction mixture can flow being arranged between the two. The path through the reaction mixture contained in the container traversed during the absorption measurement by the light emitted by the light source before it re-emerges from the container and is detected by the detector is the so-called layer thickness, which preferably lies between 0.5 and 1.5 cm. The light source and the detector are preferably assembled in a flow cell, which is connected to bypass lines carrying reaction mixture.

The light source emits over the broadest possible spectral range (continuum source) if absorption spectra are intended to be recorded. For measuring the absorption at a specific wavelength, a light source emitting in a small spectral range, more particularly a monochromatic light source, is also sufficient. The light source may also comprise two different lamps in order to cover a large spectrum. A monochromator can serve to decompose the light into individual wavelengths. By way of example, the detector can contain a vacuum photocell, a photomultiplier or a field of silicon photodiodes.

The signal detected by the detector is optionally amplified by an amplifier and evaluated in an evaluation unit (e.g. a computer). The result of the concentration of nitro and nitroso compounds determined from the measured absorption is for example displayed on a display for providing a user with this information. It can be used to regulate the amine production method or trigger an alarm signal if a specific nitro and nitroso compound concentration is exceeded. Furthermore, the evaluation unit can be programmed such that it identifies an incorrect measurement as a result of gas bubbles in the reaction mixture and discards it (i.e. it does not display it, use it to regulate the method or take account of it in any other way).

According to the invention, the catalysts do not have to be but can be separated off from the reaction mixture using at least one separation process.

The on-line monitoring of the concentration of nitro and nitroso compounds enables manual sampling and off-line analysis of nitroaromatics and nitrosoaromatics to be avoided. Manual sampling frequently represents a considerable risk and off-line analysis is complicated and time-consuming.

Since even amounts of DNT of more than 1000 ppm represent a considerable safety risk in respect of thermal decomposition and since even amounts above 30 and in particular above 100 ppm lead to increased catalyst deactivation, an (involuntary) increase in DNT can be quickly recognized by on-line monitoring of the reaction mixture and countered. Acceleration of the deactivation of the catalyst due to an increased nitroaromatics concentration and corresponding commencement of a negative spiral can be prevented in this way.

The dinitrotoluene concentration in the liquid product output from the reactor is preferably set to a value in the range from 1 to 100 ppm by weight, based on the total weight of the liquid product output from the reactor, more preferably to a value of from 2 to 50 ppm by weight, based on the total weight of the liquid product output from the reactor, and particularly preferably to a value in the range from 3 to 30 ppm by weight, based on the total weight of the liquid product output from the reactor.

Possibilities for countering an increased nitroaromatics concentration are increased introduction of fresh catalyst, a reduction in the amount of nitroaromatics continuously introduced, an increase in the reaction temperature, in the hydrogen partial pressure or in the intensity of mixing (e.g. an increase in the stirrer speed in the case of a stirred tank reactor). In the case of slightly increased nitroaromatics concentrations, preference is given firstly to increasing the introduction of fresh catalyst and, if this is not sufficient, additionally reducing the amount of nitroaromatics continuously introduced.

In a preferred embodiment of the invention, the content of nitroaromatics and nitrosoaromatics is determined on-line in the hydrogenation bath by means of a GC and a suitable computer-aided calibration model during the hydrogenation. From the GC, data on the content of nitroaromatics and nitrosoaromatics are then transmitted to the process control system via interfaces typical of process control technology, e.g. field bus. On the basis of the content of nitroaromatics and nitrosoaromatics determined, the introduction of nitroaromatic or catalyst can be regulated by means of the process control system. The on-line control of a production plant for regulating various polymerization parameters using a predictive model set up on the basis of measured spectra is known per se from U.S. Pat. No. 5,121,337 and EP-0 094 876 B1. Furthermore, EP 1 445 246 A2 describes appropriate monitoring and/or control of a nitration process.

It has been found that even small amounts of dinitrotoluene can be detected in a hydrogenation process by means of the method according to the invention. Since amounts of DNT above only 1000 ppm represent a considerable safety risk in respect of thermal decomposition and since amounts above 30 and in particular above 100 ppm lead to increased catalyst deactivation, introduction of too much DNT can be avoided automatically via the process control system by means of the on-line monitoring of the reaction mixture.

An important measure of the reliability of the instrument is the reproducibility of the analytical results. To determine this parameter, repeated analyses (usually over a period of 8 hours) are carried out on one and the same sample. Typical reproducibilities in process GC are <+/−0.5% for main components, <+/−2% for traces. However, it should be noted that the reproducibility only gives information on the magnitude of random measurement errors. The accuracy of a chromatographically determined measurement can additionally depend significantly on instrument-independent factors (e.g. construction of sampling, quality of the calibration medium used, quality of the operating gases used).

The invention is particularly advantageous since it makes a considerably improved process regime possible. In particular, the invention enables the production plant to be operated continuously close to the technical and economical optimum. A further advantage is the improvement in workplace safety.

The hydrogenation process can be carried out in any suitable way. For suitable processes and catalysts which can be used therein, reference may be made, for example, to DE-A-2 044 657, EP-A-1 138 665, WO 2005/037768, WO 00/35852, DE-A-198 57 409, EP-A-0 124 010 and PCT/EP 2009/067610 or EP 10 162 924.4, which has earlier priority and is not a prior publication.

The customary and known hydrogenation reactors are used as reactors. Examples are stirred vessels, fluidized-bed reactors, monolithic, catalytic hydrogenation reactors as described, for example, in EP-A 2 1310302, shell-and-tube reactors, bubble columns which may contain packing or loop or circular-flow reactors, e.g. loop Venturi reactors, or jet loop reactors having an internal or external circuit, as described, for example, in WO 00/35852 or DE-A-198 57 409 or WO 03/068724. A reactor as described in EP-A-0 124 010 can also be used.

Aromatic amines are preferably prepared by hydrogenation of nitroaromatics having one or more nitro groups and from 6 to 18 carbon atoms by means of the production process of the invention. The nitroaromatics are, for example, nitrobenzene, dinitrobenzenes such as 1,2-, 1,3-, 1,4-dinitrobenzene, nitrotoluenes such as o-, m-, p-nitrotoluene, dinitrotoluenes such as 2,4-, 2,6-, 2,3-, 3,4-, 2,5-dinitrotoluene, 2,4,6-trinitrotoluene, nitroxylenes such as 1,2-dimethyl-3-, 1,2-dimethyl-4-, 1,4-dimethyl-2-, 1,3-dimethyl-2-, 2,4-dimethyl-1- and 1,3-dimethyl-5-nitrobenzene, nitronaphthalenes such as 1-, 2-nitronaphthalene, 1,5- and 1,8-dinitronaphthalene, chloronitrobenzenes such as 2-chloro-1,3-, 1-chloro-2, 4-dinitrobenzene, o-, m-, p-chloronitrobenzene, 1,2-dichloro-4-, 1,4-dichloro-2-, 2,4-dichloro-1- and 1,2- dichloro-3-nitrobenzene, chloronitrotoluenes such 4-chloro-2-, 4-chloro-3-, 2-chloro-4- and 2-chloro-6-nitrotoluene, nitroanilines such as o-, m-, p-nitroaniline and any mixtures of 2 or more of the nitro compounds mentioned.

The hydrogenation in the process of the invention is preferably carried out under a pressure in the range from 5 to 50 bar, preferably at a pressure in the range from 10 to 40 bar, particularly preferably at a pressure in the range from 20 to 30 bar. The operating temperature at which the hydrogenation of dinitrotoluene to toluenediamine is carried out is generally in the range from 50 to 250° C., preferably in the range from 80 to 200° C., particularly preferably in the range from 105 to 130° C.

In a further preferred embodiment of the invention, the process of the invention is operated with additional monitoring of the concentration of the partially hydrogenated intermediate aminonitrotoluene, hereinafter referred to as ANT for short, with an ANT concentration in the range from 0 to 2000 ppm, preferably an ANT concentration in the range from 0.5 to 1000 ppm, particularly preferably an ANT concentration in the range from 1 to 200 ppm, being set in the region between the reactor and the product isolation unit. Setting of the concentration of this partially hydrogenated intermediate in said regions firstly allows a further reduction in catalyst deactivation and secondly allows a further reduction in by-product formation. In general, the concentrations of DNT and ANT run largely parallel.

Many catalysts are possible for the preparation of TDA.

In a first general embodiment of the invention, the process of the invention as described above is carried out in the presence of a catalyst, preferably a nickel-comprising catalyst, in particular in the presence of a supported catalyst comprising nickel alone or together with at least one metal of transition group I, V, VI and/or VIII of the Periodic Table as active component. The catalysts used according to the invention can be produced industrially by applying nickel and optionally at least one of the abovementioned additional metals to a suitable support.

In a preferred embodiment of the invention, the catalyst has a nickel content in the range from 0.1 to 99% by weight, preferably from 1 to 90% by weight, particularly preferably from 25 to 85% by weight and very particularly preferably from 60 to 80% by weight, based on the total weight of the catalyst.

Preference is given to using palladium, platinum, rhodium, iron, cobalt, zinc, chromium, vanadium, copper, silver or a mixture of two or more thereof as metals of transition group I, II, V, VI and/or VIII of the Periodic Table.

In a preferred embodiment of the invention, the catalyst comprises nickel and platinum. In a further preferred embodiment of the Invention, the catalyst comprises nickel and aluminum; in a further particularly preferred embodiment, the catalyst comprises nickel, palladium and iron.

As support materials, preference is given to using activated carbon, carbon black, graphite or oxidic support components such as silicon dioxide, silicon carbide, kieselguhr, aluminum oxide, magnesium oxide, titanium dioxide, zirconium dioxide and/or hafnium dioxide or a mixture of two or more thereof, particularly preferably zirconium dioxide, $ZrO_2$, $HfO_2$ and/or $SiO_2$, $ZrO_2$ and/or $SiO_2$, $ZrO_2$, $HfO_2$.

The supports used are preferably mesoporous and have an average pore diameter of from 35 to 50 nm and a specific surface area of from 50 to 250 m$^2$/g. The surface area of the support is determined by the BET method by $N_2$ adsorption, in particular in accordance with DIN 66131. The determination of the average pore diameter and the pore size distribution is carried out by Hg porosimetry, in particular in accordance with DIN 66133.

The application of nickel and optionally at least one further metal can be achieved by the usual suitable methods which are known to a person skilled in the field of catalyst technology. The supports, coated by coprecipitation or impregnated with the metal or metal salt are subsequently dried and calcined by known methods. The coated supports are then activated by treatment in a gas stream comprising free hydrogen.

This activation usually takes place at temperatures in the range from 30 to 600° C., preferably in the range from 80 to 150° C. and particularly preferably at 100° C. The gas stream preferably comprises from 50 to 100% by volume of hydrogen and from 0 to 50% by volume of nitrogen. The catalyst produced for use according to the invention has, after reduction at 100° C. for one hour, a degree of reduction of at least 70%.

The supported catalysts obtained in this way generally have a nickel metal surface area of from about 10 to about 50 m$^2$/g, preferably from about 20 to about 60 m$^2$/g. The nickel content of the catalysts used in the process of the invention is generally in the range from 0.1 to 99% by weight, preferably in the range from 1 to 90% by weight, particularly preferably in the range from 25 to 85% by weight, based on the total weight of the catalysts used.

Suitable catalysts of this embodiment are described, for example, in the documents EP 1 161 297 A1 and EP 1 165 231 A1.

In a second embodiment of the invention, activated nickel catalysts as described, for example, in WO 2008/145179 A1 are used in the process of the invention. Accordingly, activated nickel catalysts based on an Ni/Al alloy, which can comprise one or more metals selected from the group consisting of Mg, Ce, Ti, V, Nb, Cr, W, Mn, Re, Fe, Ru, Co, Rh, Ir, Pt, Cu, Ag, Au and Bi, are used in a preferred embodiment of the invention. The degree of doping is in the range from 0.05% by weight to 20% by weight for each doping element. The average particle size of the catalysts used is <25 μm.

In a third embodiment of the invention, catalysts described, for example, in WO 2008/138784 A1 are used in the process of the invention. The invention therefore further provides, in a preferred embodiment of the invention, for the use of hydrogenation catalysts comprising a mixture of nickel, palladium and an additional element selected from the group consisting of cobalt, iron, vanadium, manganese, chromium, platinum, iridium, gold, bismuth, molybdenum, selenium, tellurium, tin and antimony as active component on a support for preparing aromatic amines by catalytic hydrogenation of the corresponding nitro compounds, in particular for preparing toluenediamine by hydrogenation of dinitrotoluene. The additional element is preferably selected from the group consisting of cobalt, iron, vanadium, bismuth and tin.

As supports for the catalyst it is possible to use the materials which are customary and known for this purpose. Preference is given to using activated carbon, carbon black, graphite or metal oxides, preferably hydrothermally stable metal oxides such as $ZrO_2$, $TiO_2$, $Al_2O_3$. In the case of graphite, HSAG (high surface area graphite) having a surface area of from 50 to 300 m$^2$/g is particularly preferred. Particular preference is given to activated carbons, in particular physically or chemically activated carbons, or carbon blacks such as acetylene black.

The hydrogenation catalysts according to the invention preferably comprise from 0.5 to 5% by weight of palladium, from 10 to 20% by weight of nickel and from 0.5 to 5% by weight of the additional element.

In the process of the invention, 2,4-DNT or industrial mixtures thereof which additionally comprise 2,6-DNT, with these mixtures preferably comprising up to 35% by weight, based on the total mixture, of 2,6-DNT with proportions of from 1 to 4% of vicinal DNT and from 0.5 to 1.5% of 2,5- and 3,5-DNT, are hydrogenated to the corresponding amine. The DNT isomers are frequently used in the isomer ratio obtained in the double nitration of toluene.

In the process of the invention, the 2,4-DNT or the 2,4-DNT/2,6-DNT mixture can be used in pure form, as a mixture with water, as a mixture with water and an alcoholic solvent or as a mixture with water, an alcoholic solvent and a catalyst-reactivating additive. Likewise, catalyst, water and/or alcoholic solvent or mixtures thereof can be metered in together with or separately in addition to the DNT.

As can be seen from what has been said above, the hydrogenation can be carried out in the absence or in the presence of an alcoholic solvent and a catalyst-activating additive in the process of the invention.

If an alcoholic solvent and a catalyst-reactivating additive are used, it is of course also possible to add mixtures of two or more thereof.

Alcoholic solvents used are lower aliphatic alcohols having from 1 to 6 carbon atoms, preferably methanol, ethanol or propanol alone or a mixture of two or more thereof.

As catalyst-activating additives, preference is given to using aprotic solvents, in particular acetone, dimethylformamide, dioxane or tetrahydrofuran or a mixture of two or more thereof.

The amount of alcoholic solvent used and of the catalyst-reactivating additives is not restricted in any particular way in the process of the invention and can be chosen freely by a person skilled in the art depending on requirements.

In a preferred embodiment of the invention, the hydrogenation is carried out in a three-phase mixture of hydrogen-comprising gas phase, suspended catalyst and liquid phase comprising from 0 to 40% by volume of an alcohol, from 10 to 60% by volume of water and from 20 to 70% by volume of TDA, as defined above. The catalyst content is from about 0.1 to 15% by weight, preferably from 2 to 8% by weight, based on the total weight of the three-phase mixture used.

The result of the particular concentration of nitro and nitroso compounds is, for example, indicated on an information notice of a user. It can be employed for regulating the amine production process or trigger an alarm signal if a particular nitro and nitroso compound concentration is exceeded.

The apparatus of the invention makes automatic pseudo-continuous on-line measurement of the concentration of nitro and nitroso compounds in the reaction mixture possible. The catalyst consumption can be optimized and thus reduced in an advantageous way by means of the above-described regulation method based on the concentration measurement.

The invention is illustrated below with the aid of the examples and the drawings.

Figure 1:
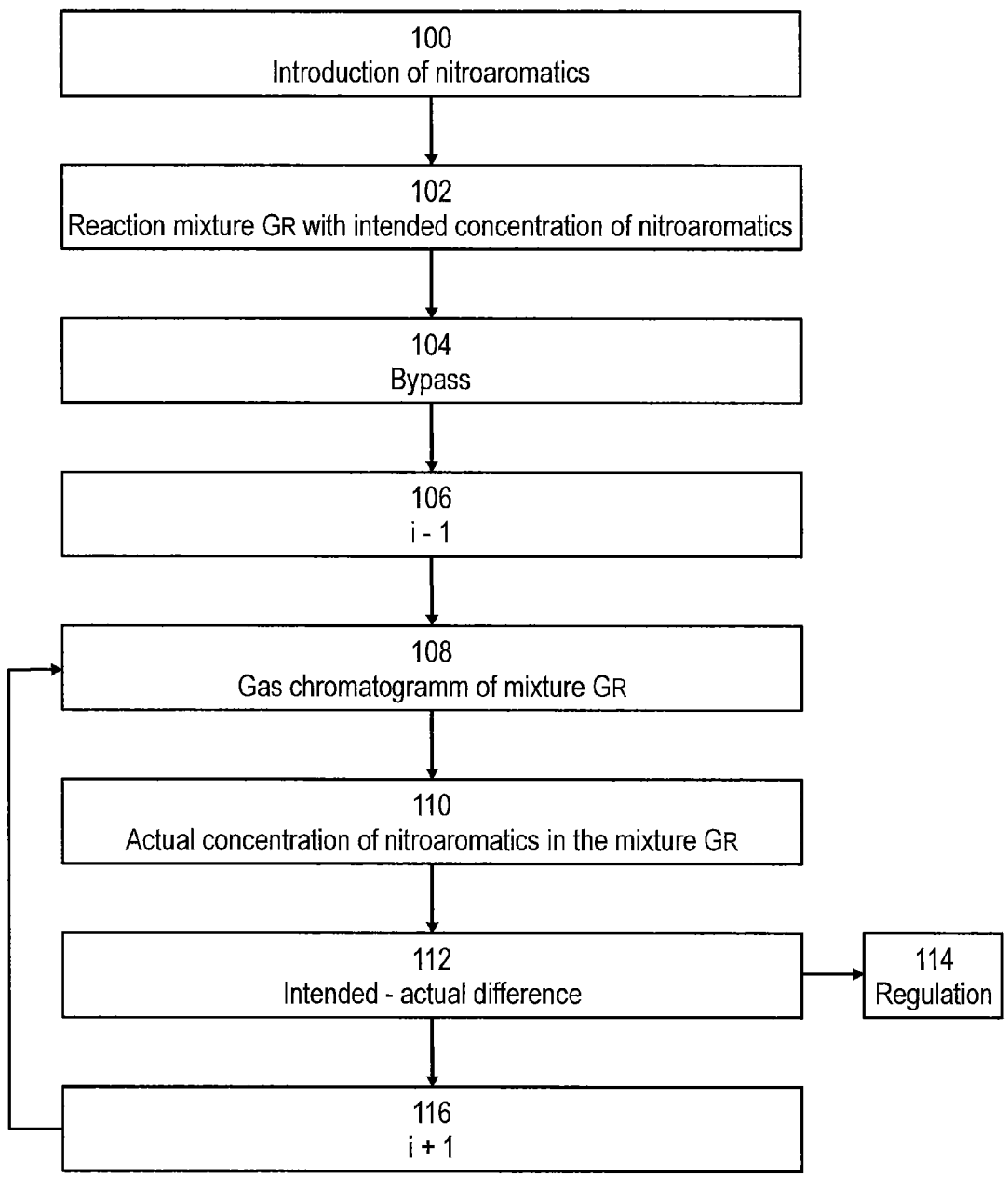
FIG. 1 is a flow diagram of an embodiment of a method according to the invention for determining the nitroaromatics concentration in various hydrogenation baths.
Figure 2:
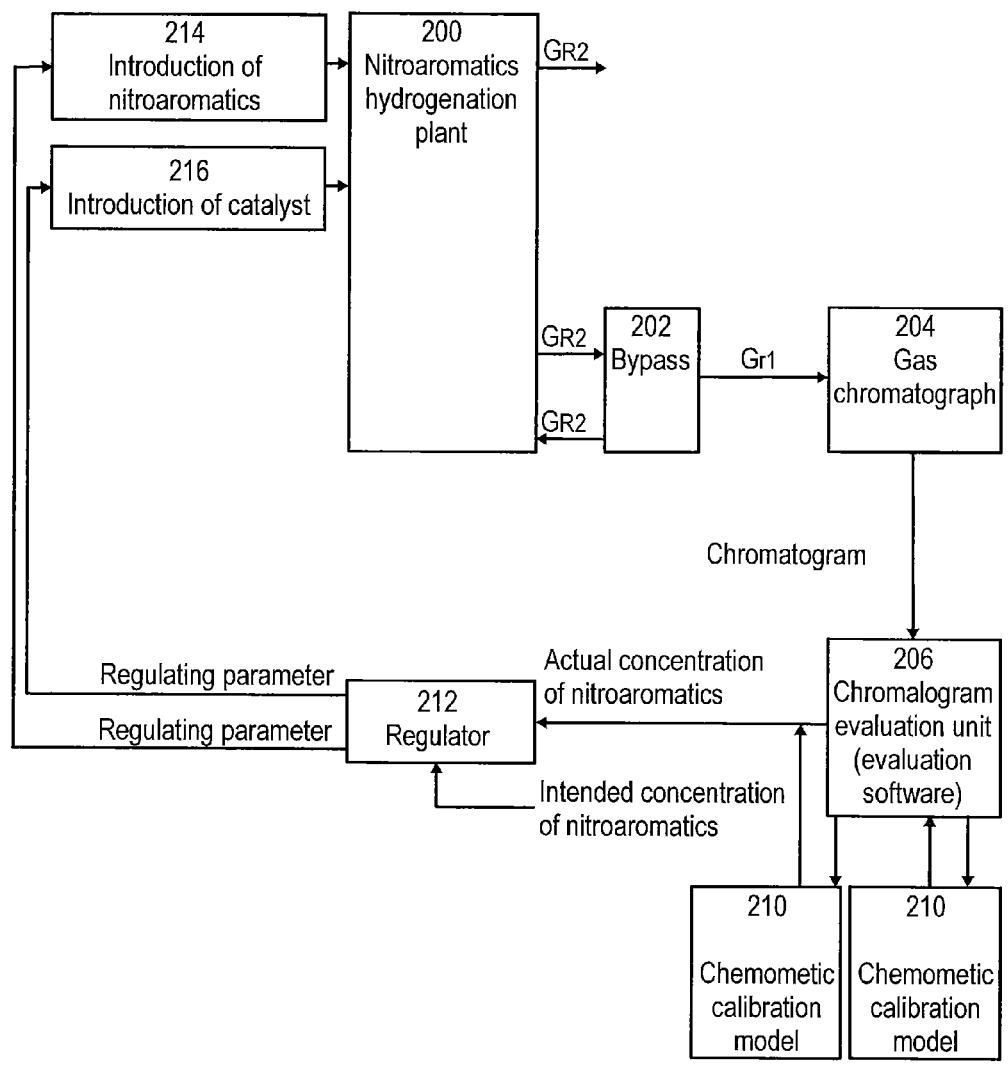
FIG. 2 is a block diagram of a hydrogenation plant with an embodiment of the regulation according to the invention.
Figure 3:
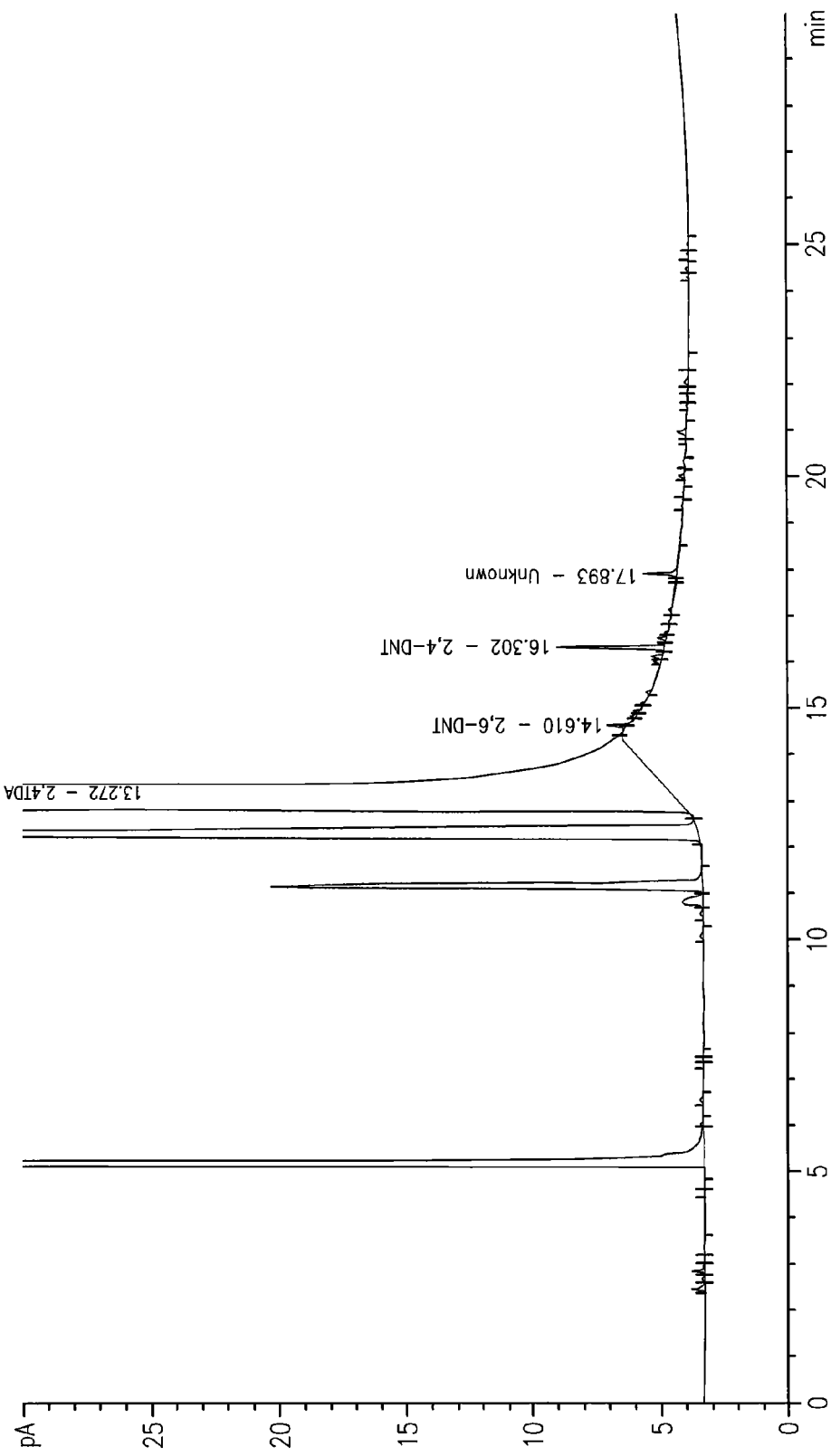

In the drawings:

FIG. 1 shows a flow diagram of an embodiment of a method according to the invention for determining the nitroaromatics concentration in various hydrogenation baths, FIG. 2 shows a block diagram of a hydrogenation plant with an embodiment of the regulation according to the invention, FIG. 3-FIG. 7 show chromatograms of the reaction mixture with the various isomers; analyzed by method 3a, 3b and 3c:

FIG. 3 (analysis by method 3a)

Figure 4:
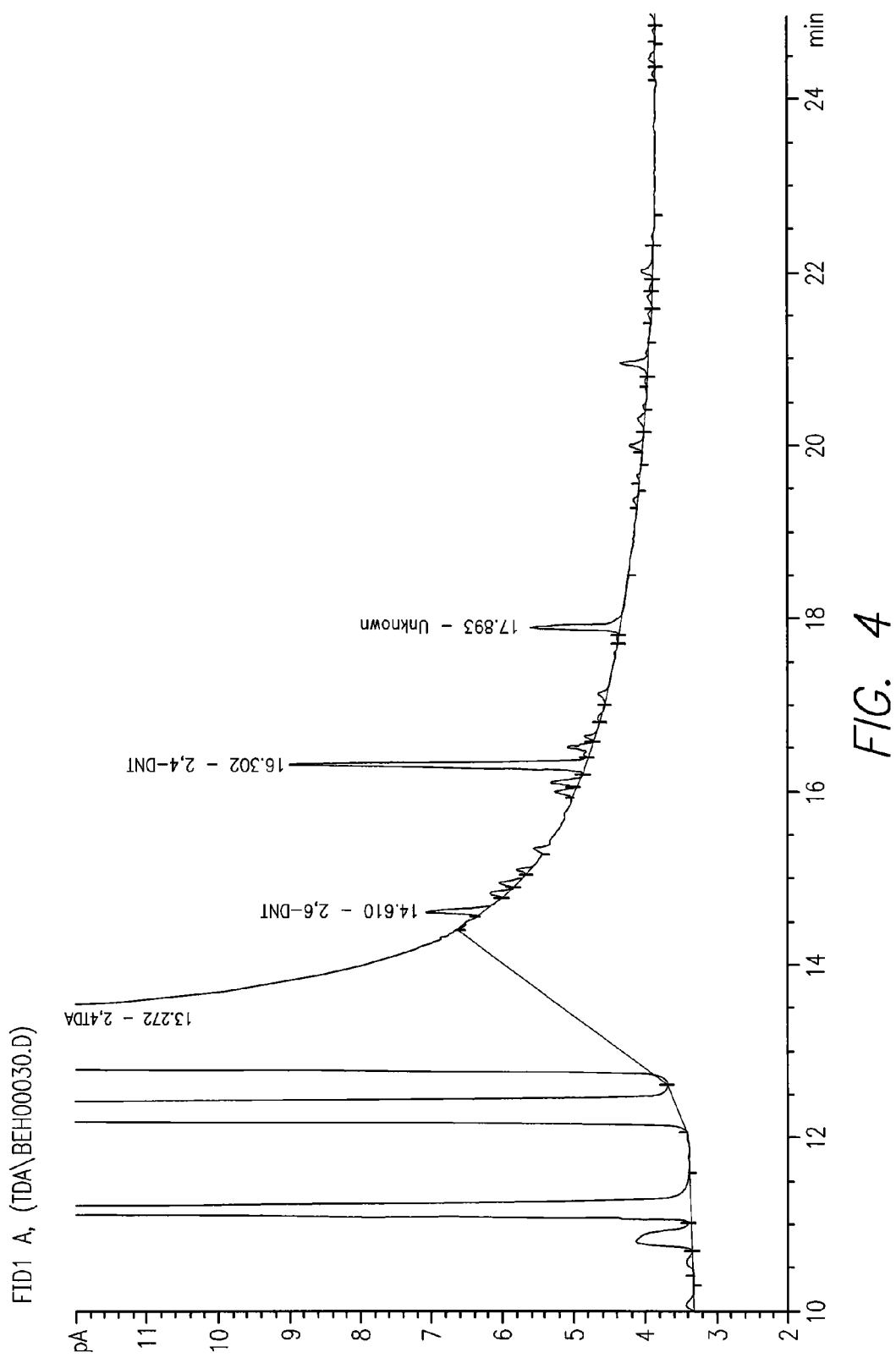

FIG. 4 (analysis by method 3a—enlargement of a section)

Figure 5:
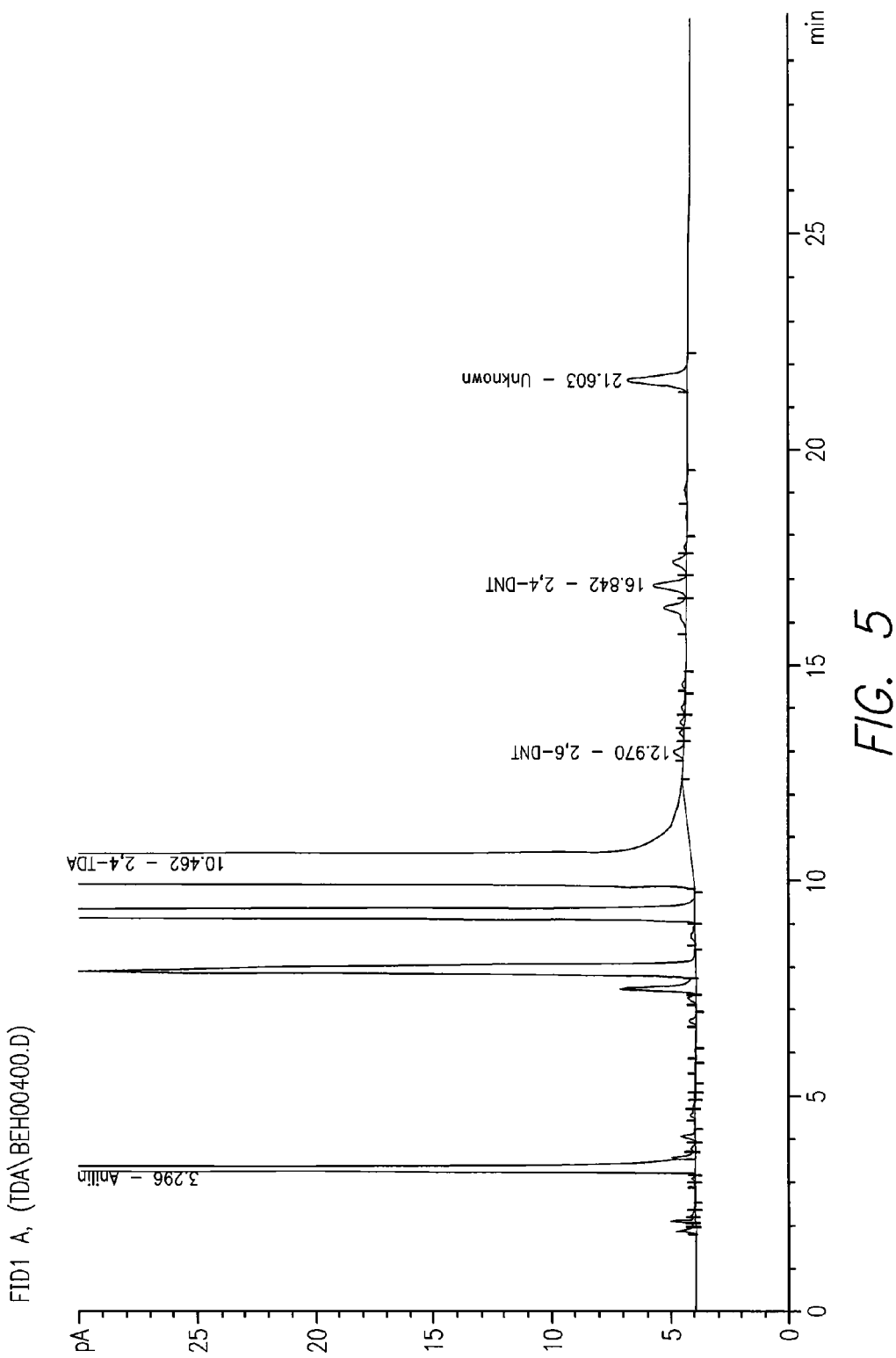
FIGS. 5-6 are chromatograms of the reaction mixture with the various isomers analyzed by method 3b.

FIG. 5 (analysis by method 3b)

Figure 6:
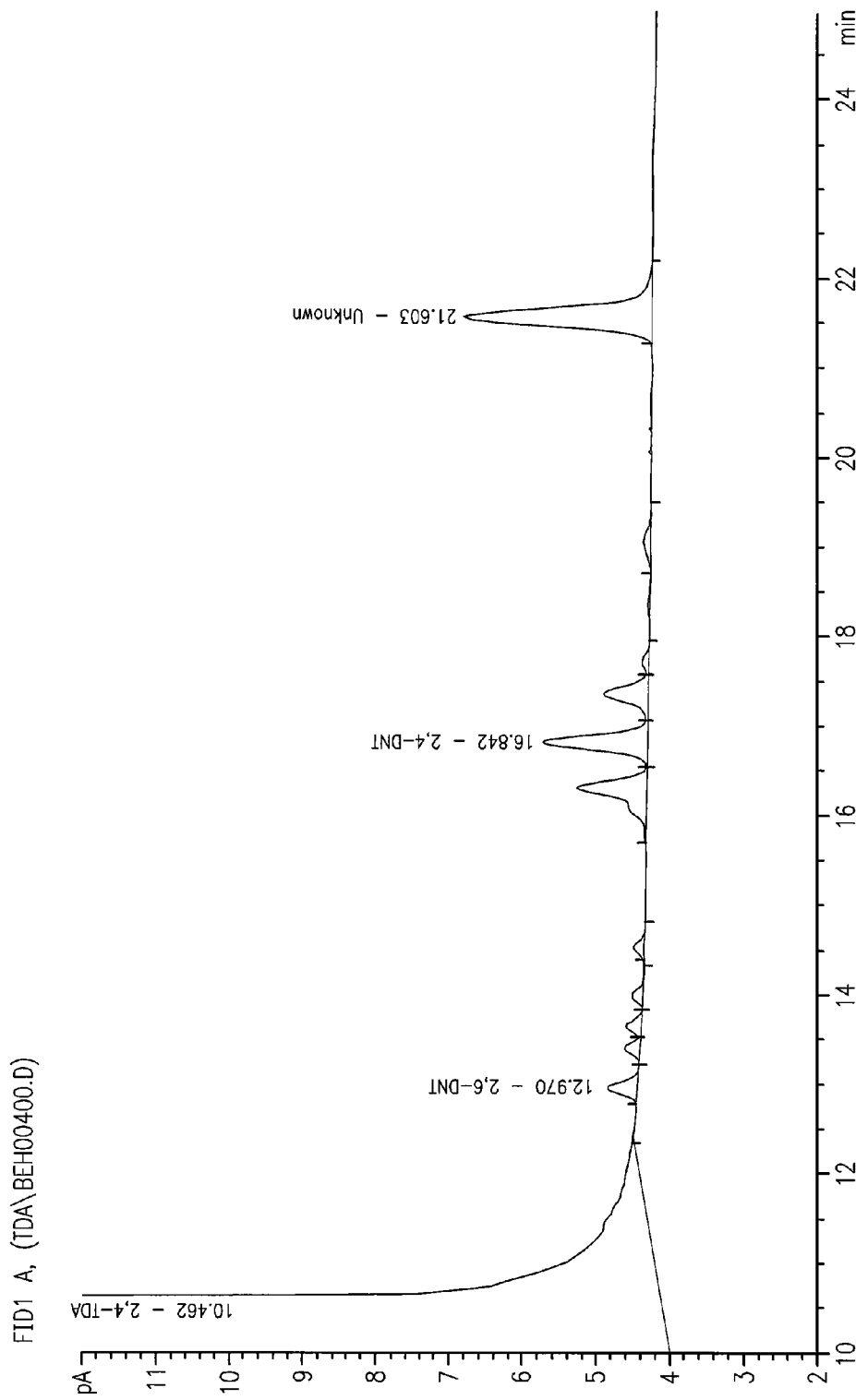

FIG. 6 (analysis by method 3b—enlargement of a section)

Figure 7:
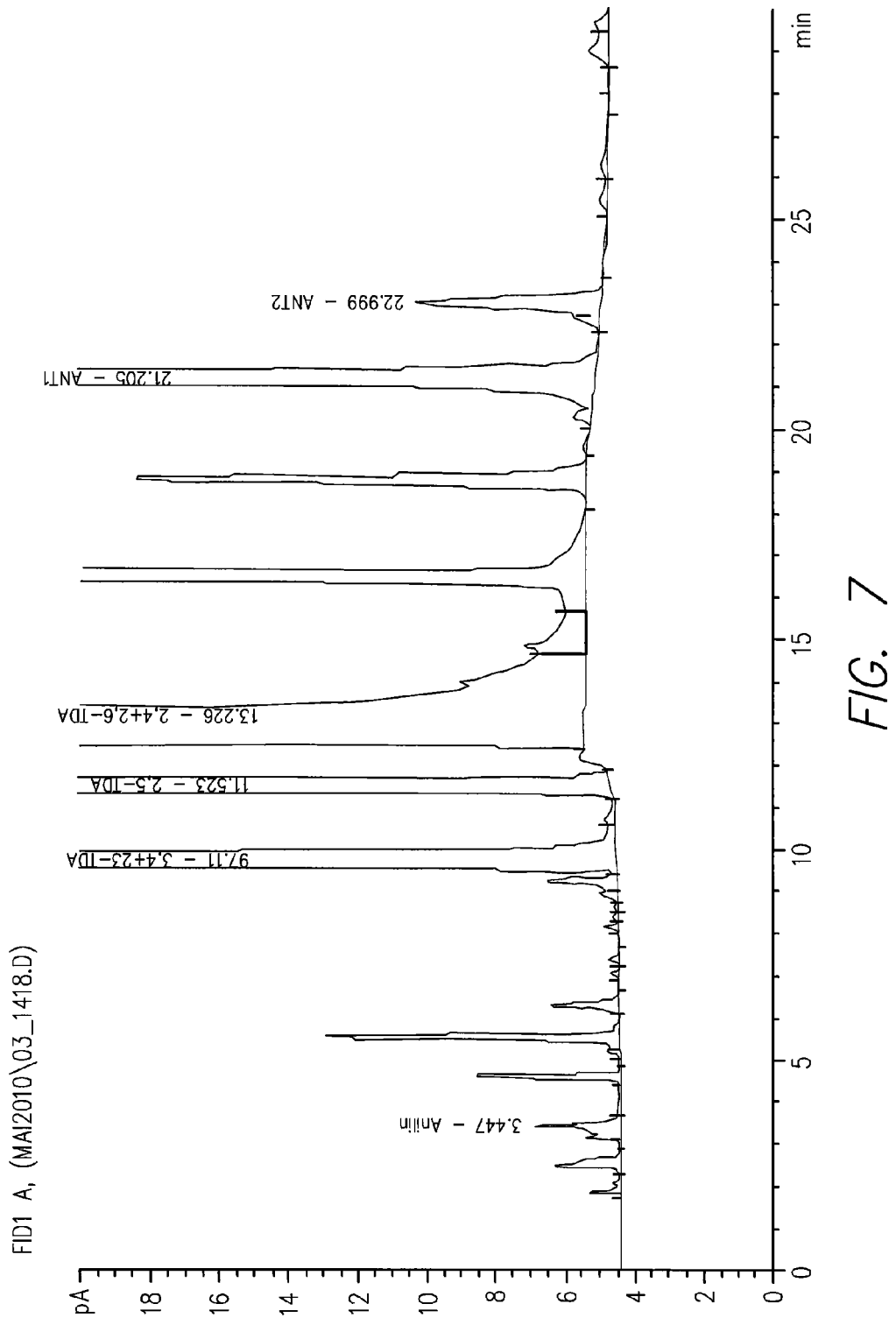
FIG. 7 is a chromatogram of the reaction mixture with the various isomers analyzed by method 3c.

FIG. 7 (analysis by method 3c)

Figure 9:
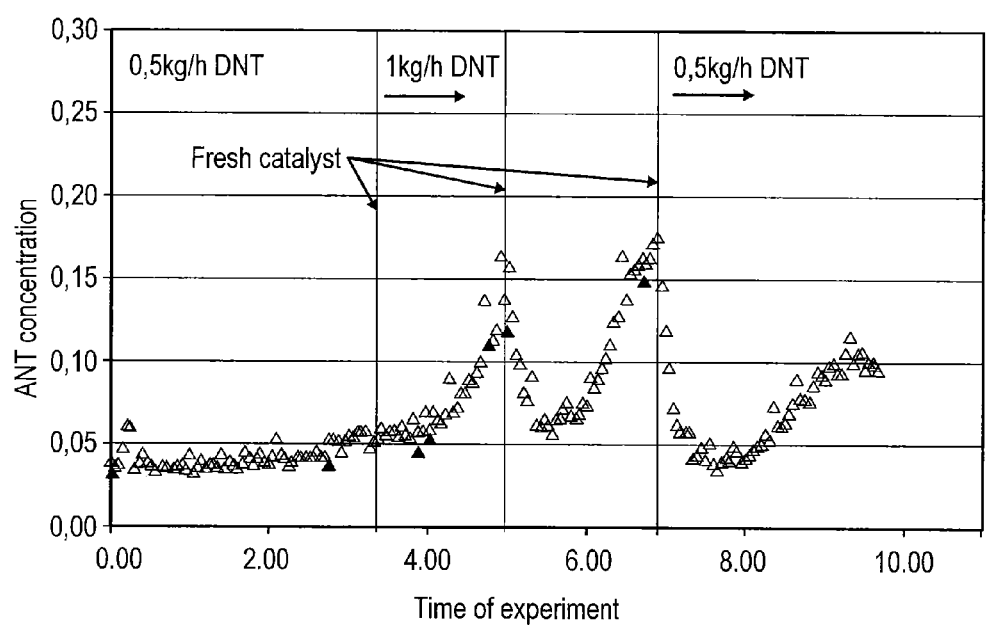
FIG. 9 shows ANT concentrations in percent by weight measured by means of on-line GC (white symbols) and ANT concentrations in percent by weight determined by means of off-line GC (black symbols) as a function of the time of the experiment in days.

FIG. 8 schematically shows a plant for carrying out the process of the invention, FIG. 9 shows ANT concentrations in percent by weight measured by means of on-line GC (white symbols) and ANT concentrations in percent by weight determined by means of off-line GC (black symbols) as a function of the time of the experiment in days.

In step 100 in FIG. 1, nitroaromatics are fed into the hydrogenation bath 102 which comprises the reaction mixture $G_R$ comprising the catalyst, the mixture of aromatic amine and water and an atmosphere of hydrogen. The reaction mixture comprises, depending on the activity of the catalyst and the rate of introduction, small amounts of nitroaromatics or aminonitroaromatics which should not exceed a particular intended concentration.

Part of the hydrogenation bath is branched off via an attached bypass 104. In step 106, the index i is initialized. In step 108, the chromatogram of the reaction mixture $G_R$ is recorded on-line. This is effected, for example, by an on-line process GC measurement. This results in step 110 in the actual concentration of the mixture $G_R$. In step 112, the difference between the intended and actual values of the concentrations of nitroaromatics in the reaction mixture $G_R$ is formed. On the basis of this difference, after-regulation of the introduction of nitroaromatics is carried out in step 114. In step 116, the index i is incremented. A chromatogram is subsequently measured again in step 108. This procedure is repeated until the actual nitroaromatics concentration is in the range from 3 to 30 ppm for all reaction mixtures $G_R$ measured. The index i is then reset, so that the actual nitroaromatics concentrations of all reaction mixtures $G_R$ measured are determined continuously within relatively short time intervals, e.g. a few minutes, and the corresponding after-regulation can be carried out close to real time.

FIG. 2 shows a hydrogenation plant for nitroaromatics 200 for preparing mixtures of aromatic amines and water $G_{R2}$. Sampling, achieved by means of a bypass 202 with liquid metering valve through which part of the reaction mixture $G_{R2}$ continually flows, can be carried out in the product stream in the region between reactor and product isolation unit (preferably with filter) or downstream of the product isolation unit (preferably crossflow filter). The bypass can be isolated from the product stream by means of two valves (e.g. for maintenance work on the gas chromatograph). Sampling (gas chromatograph) 204 comprises a pressure-stable and heat-resistant sampling valve.

The analysis of the measured chromatogram gives, after chromatogram analysis 206 and/or evaluation by means of chemometric calibration model 210, which sends the results either back to the evaluation unit or directly to the regulator 212, the actual concentration of the reaction mixture $G_{R1}$. This actual concentration of nitroaromatics is transmitted to a regulator 212 together with the intended concentration of nitroaromatics of the reaction mixture $G_{R1}$. From the difference between the actual concentration and the intended concentration, the regulator 212 determines a regulating variable for after-regulation of the introduction of nitroaromatics 214 and/or the introduction of the catalyst 216 of the nitroaromatics hydrogenation plant 200.

The regulator 212 can be realized by a process control system of the nitroaromatics hydrogenation plant 200. As an alternative, it is also possible to display the measurement results on, for example, a display unit of a control console of the nitroaromatics hydrogenation plant 200, so that the introduction of nitroaromatics 214 and/or the introduction of catalyst 216 can be after-regulated manually.

FIG. 8 schematically shows a plant for carrying out the process of the invention.

The reactor 1 is equipped in its upper region with a downward-directed driving jet nozzle 2 via which the reaction mixture is injected into the reactor via an external loop 3. Below the driving jet nozzle 2, there is a central plug-in tube 4 arranged in the longitudinal direction of the reactor and below the plug-in tube 4 there is an impingement plate 5. A field tube heat exchanger 6 is present in the interior of the reactor 1. In the preferred variant depicted in the figure, dinitrotoluene, DNT, is fed via an annular gap at the outer wall of the driving jet nozzle 2 configured as a two-jet nozzle into the gas space above the surface of the liquid in the reactor 1.

Hydrogen $H_2$ is, in the preferred variant shown in the figure, injected into the lower region of the reactor 1 via a ring distributor and additionally into the external loop 3 in the vicinity of the point at which the reaction mixture is taken off from the bottom of the reactor. In the preferred embodiment depicted in the figure, the reaction mixture is conveyed in the external loop via a pump P which is designed so that it can pump up to 20% by volume of gas through a crossflow filter 7 for separating off the catalyst. The reaction mixture is subsequently conveyed through a heat exchanger W, which is preferably configured as a shell-and-tube heat exchanger, arranged in the external loop. Steam is taken off via line 8 from the heat exchanger W arranged in the external loop and combined with steam via line 9 from the field tubes which are supplied with water, $H_2O$, fed to a separator tank 10 and taken off as steam having a gauge pressure of 4 bar via line 11.

Sampling for the on-line gas chromatography can be located in a bypass for the liquid product output between reactor 1 and product isolation unit 7 (crossflow filter), preferably with an additional filter (e.g. membrane filter) (corresponds to option A) or in a bypass for the liquid product output downstream of the product isolation unit 7 (corresponds to option B).

The invention is illustrated by the following examples.

EXAMPLES

Example 1

A cylindrical loop reactor having an external circuit which is driven by two centrifugal pumps arranged in series and opens into a driving jet nozzle arranged centrally at the top of the reactor, a concentric plug-in tube and an impingement plate in the lower part of the reactor for redirecting the loop flow (internal circuit) (for the functional principle, cf. WO 2000/35852 A1) is used. The reaction volume of the reactor is about 14 $m^3$. The reactor is provided with a bundle of parallel field tubes to remove the heat of reaction. The amount of cooling water fed into the field tubes is set so that the temperature in the reactor is maintained at about 120° C. To maintain the loop flow, a volume flow of 600 $m^3$/h is circulated in the external product circuit, as a result of which a pressure drop of about 2.5 bar is established over the driving jet nozzle. The reactor comprises about 12 $m^3$ of a liquid hydrogenation bath. This consists essentially of a mixture of TDA and water in a mass ratio of 0.58:0.42 in which about 5% by weight of a metallic Ni catalyst supported on $SiO_2$ and $ZrO_2$ (produced as described in example 2 of EP 1 161 297 and comminuted by means of a stirred ball mill; here, 10% by volume of the catalyst consists of particles having a diameter of 5 about 5 μm, 50% by volume are 5 about 10 μm, and 90% by volume are 5 about 15 μm, measured by means of laser light scattering (Malvern Mastersizer S) after stirring in water) is suspended and hydrogen is additionally dissolved.

The surface of the liquid is just below the opening of the driving jet nozzle. Above this, there are about 2 $m^3$ of a gas atmosphere whose hydrogen content is set to from 90 to 95% by volume (in addition to inert gases such as $N_2$) by continuous discharge of a small offgas stream. 7.5 t/h of molten DNT heated to about 80° C., which comprises a mixture of the 2,4- and 2,6-DNT isomers in a ratio of about 80:20 and about 5% of the other DNT isomers and traces of mononitrotoluene, is injected by means of a diaphragm metering pump into the gas space of the reactor. A pressure of 25 bar is set in the reactor by simultaneous introduction of about 0.5 t/h of hydrogen (diluted with about 2 kg/h of $N_2$). 95% of the hydrogen are introduced into the hydrogenation bath via a nozzle ring above the impingement plate and 5% are introduced at the reactor outlet. The reaction proceeds under largely isothermal conditions: in the total reactor, the reaction temperature is always in the range from 116 to 126° C. In addition, 625 kg/h of a suspension of the abovementioned catalyst in water (partly separated off from the hydrogenation product in the work-up section) are metered in, likewise continuously, via a diaphragm pump. The amount of catalyst present in this suspension is varied in a targeted manner in the range from 0 to 5 kg/h to adjust the DNT concentration and is on average about 1 kg/h.

To keep the level of liquid in the reactor constant, an appropriate amount of hydrogenation product is taken off continuously from the external product circuit on the pressure side of the 2nd centrifugal pump and fed into a lamellar clarifier having a liquid volume of about 50 $m^3$ and a gas volume of about 10 $m^3$. The catalyst can concentrate in the lower region of this. 18 standard $m^3$/h of an appropriately thickened suspension are then recirculated to the suction side of the first centrifugal pump. At the same time, about 8.6 t/h of hydrogenation product are taken off from the lamellar clarifier via an overflow. This hydrogenation product comprises about 4.9 t/h of TDA (having an isomer distribution corresponding to the DNT used), about 0.1 t/h of low and high boilers (in a ratio of about 20:80) and about 3.6 t/h of water and up to about 1 kg/h of catalyst (mainly fines). The hydrogenation product goes, like the hydrogenation product from other reactors, via a pressure reduction valve into a common intermediate vessel and from this is fed continuously to work-up by distillation. The parts which come into contact with product are partly made of black steel (generally St37) and partly of stainless steel (1.4571).

To determine the content of DNT and ANT in the hydrogenation bath, a solids-free filtrate stream is conveyed continuously from the line from the external product circuit of the loop reactor to the lamellar clarifier via a bypass with filter membrane and samples are taken from this on-line by means of a liquid metering valve at intervals of about 1 hour. The concentration of the nitro compounds comprised is then determined by means of on-line gas chromatography. The DNT concentration is set in the range from 3 to 30 ppm and the ANT concentration is set in the range from 1 to 200 ppm, by adjustment of the catalyst concentration in the aqueous suspension (see above) fed to the reactor.

The reactor can be operated under the stated conditions for 3 months without appreciable interruptions. No appreciable catalyst deactivation is observed during this time.

Example 2

A stirred tank reactor (diameter: 2.8 m, height: 4.7 m, volume: 23 $m^3$, material: St37) with cooling coils fixed by means of fine connections in the region of the reactor wall and a double inclined blade stirrer is used: the larger upper set of inclined blades pushes the hydrogenation bath downward in the interior of the reactor and this then flows upward again along the cooling coils; the lower set of inclined blades, on the other hand, sucks in the thickened suspension flowing back from the lamellar clarifier likewise used here and pushes it upward into the flow generated by the upper set of blades. The amount of cooling water fed into the cooling coils is set so that the temperature in the reactor is maintained in the range from 116 to 126° C. The reactor comprises about 18 m³ of a liquid hydrogenation bath. This consists essentially of a mixture of TDA and water in a mass ratio of 0.58:0.42, in which about 5% by weight of the metallic Ni catalyst supported on $SiO_2$ and $ZrO_2$, as mentioned in example 1, is suspended and hydrogen is additionally dissolved. Above the surface of the liquid, there are about 5 m³ of a gas atmosphere whose hydrogen content is set to from 90 to 99% by volume (in addition to inert gases such as $N_2$) by continuous discharge of a small offgas stream.

5 t/h of molten DNT heated to about 80° C., comprising a mixture of 2,4- and 2,6-DNT isomers in a ratio of about 80:20 and about 5% of the other DNT isomers and traces of mononitrotoluene are fed by means of a diaphragm metering pump into a funnel which is open to the gas space and conveys the DNT downward via a line and between the sets of inclined blades into the hydrogenation bath. A pressure of 25 bar is set in the reactor by simultaneous introduction of about 330 kg/h of hydrogen (diluted with about 2 kg/h of $N_2$). The hydrogen is introduced into the hydrogenation bath via a nozzle ring installed centrally between the two sets of inclined blades of the stirrer and fastened there by means of fine connections. The reaction proceeds under largely isothermal conditions. In addition, 435 kg/h of a suspension of the abovementioned catalyst in water (partly separated off from the hydrogenation product in the work-up section) are introduced, likewise continuously, by means of a diaphragm pump. The amount of catalyst comprised in this suspension is varied in a targeted manner in the range from 0 to 5 kg/h to adjust the DNT concentration and is on average barely 1 kg/h.

To keep the level of liquid in the reactor constant, an appropriate amount of hydrogenation product is taken off continuously via an overflow and fed to a lamellar clarifier having a liquid volume of about 16 m³ and a gas volume of about 4 m³. The catalyst can concentrate in the lower region of this. About 30 standard m³/h of an appropriately thickened suspension are then sucked back into the stirred vessel by means of the lower set of blades of the inclined blade stirrer. At the same time, about 5.8 t/h of hydrogenation product are taken from the lamellar clarifier via an overflow. This hydrogenation product comprises about 3.3 t/h of TDA (with an isomer distribution corresponding to that of the DNT used), about 0.07 t/h of low and high boilers (in a ratio of about 10:60) and about 2.4 t/h of water and up to 1 kg/h of catalyst (mainly fines). The hydrogenation product goes, like the hydrogenation products of other reactors, via a pressure reduction valve into a joint intermediate vessel and from this is fed continuously to work-up by distillation.

To determine the content of DNT and ANT in the hydrogenation bath, a solids-free filtrate stream is conveyed continuously from the line to the lamellar clarifier via a bypass and samples are taken from this on-line by means of a liquid metering valve at intervals of about 1 hour. The concentration of the nitro compounds comprised is then determined by means of on-line gas chromatography. The DNT concentration is set in the range from 3 to 30 ppm and the ANT concentration is set in the range from 1 to 200 ppm, by adjustment of the catalyst concentration in the aqueous suspension (see above) fed to the reactor.

The reactor can be operated under the stated conditions for 3 months without appreciable interruptions. No appreciable catalyst deactivation is observed during this time.

Example 3

In a 5 liter pilot reactor, dinitrotoluene was hydrogenated over a Pt—Ni/C catalyst at a pressure of from 20 to 25 bar and a temperature of from 125 to 135° C. The concentration of dinitrotoluene and aminonitrotoluene in the reaction mixture was determined by on-line GC measurements.

The reaction mixture was passed through a catalyst removal unit (membrane filter) and the catalyst present was separated off from the product. The catalyst-free product stream was conveyed through a metering valve. The metering valve was connected to a gas chromatograph (manufacturer: Agilent Technologies, Type 6890). A sample was analyzed every hour by means of this laboratory GC with on-line construction.

The experiment was started using a low space velocity over the catalyst (0.5 kg/h of DNT) and this was increased after a certain time. FIG. 9 shows ANT concentrations measured by means of on-line GC (white symbols) and ANT concentrations determined by means of off-line GC (black symbols) as a function of the time of the experiment in days. At high DNT flows, the catalyst is poisoned (deactivated) and the concentration of ANT increases. After addition of fresh catalyst, the ANT concentration decreases again. The values determined by means of on-line and off-line GC correlate.

The use of the on-line measurement enabled fresh catalyst to be introduced in good time. The off-line results were available only with a time delay due to sampling and sample transport (from the pilot reactor to the laboratory). The personnel requirement was reduced by means of the on-line measurement.

Gas Chromatography
The methods below were used for analysis.
Laboratory Method (Method 1):
Instrument: GC 5890 (Agilent Technologies) with sampler
Detector: thermal conductivity detector
Separation column: Restek Rtx 5 Amine, length 30 m, internal diameter 0.32 mm, film thickness 1 µm.
Carrier gas: helium
Carrier gas pressure: 90 kPa
Split: 1:40
Temperature (injector): 200° C.-20° C. steps—300° C. 220° C.
Column oven: start temp.: 125° C.-5° C./min to 285° C.-40 min
Injection volume: 0.6 µl
Sample is diluted with aniline (ratio 1:4) before introduction
Automated Laboratory Method (Method 2):
Laboratory Gas Chromatograph:
Instrument GC 6890 (Agilent Technologies) modified with an automated liquid metering valve (Siemens AG)
Detector: flame ionization detector
Separation column: Rtx5 Amine, length 30 m, internal diameter 0.32 mm, film thickness 1.5 µm
Carrier gas: helium
Carrier gas pressure: 90 kPa, constant pressure
Amount introduced: 0.5 µl, split flow 70 ml/min
Injector temperature: 200° C.
Detector temperature: 300° C.
Oven temperature program: Start 125° C. (1 min), 5° C./min, 285° C. (30 min)
Automated Laboratory Method (Methods 3a & 3b & 3c)
Laboratory Gas Chromatograph:

Instrument: GC 6890 (Agilent Technologies) modified with an automated liquid metering valve (Siemens AG)
Detector: flame ionization detector
Separation column: Rtx5 Amine, length 30 m, internal diameter 0.53 mm, film thickness 3 μm
Carrier gas: helium
Injector temperature: 240° C.
Detector temperature: 300° C.
Split 1: 20 (80 ml/min)
Injection volume: 0.6 μl
Method 3a:
Helium 4 ml/min 30 kPa constant flow
Temperature ramp: 130° C. @ 1 min→285° C. at 5° C./min
Method 3b:
Helium 4 ml/min 36 kPa constant flow
Isothermal: 30 min @ 180° C./baking 30 min @ 250° C.
Method 3c:
Helium 4 ml/min 30 kPa constant flow
Temperature ramp: 170° C. @ 30 min→280° C. at 20° C./min

The invention claimed is:

1. A process for preparing aromatic amines by hydrogenation of nitroaromatics in the presence of catalysts, forming a fluid, amine-comprising reaction mixture in a reactor, wherein chromatographic analysis of the reaction mixture or a measurement of the absorption of IR- and/or VIS-radiation through the reaction mixture is carried out to determine the concentration of nitro and nitroso compounds in the reaction mixture, with the result of the determination of the concentration of nitro and nitroso compounds being used for process control or regulation of the hydrogenation, wherein samples are fed on-line via a bypass to the chromatograph and wherein the bypass is equipped with an automated liquid metering valve for sampling, optionally with upstream particle filter.

2. The process according to claim 1, wherein to determine the concentration of the nitro and nitroso compounds, a gas chromatogram of the reaction mixture is produced and evaluated.

3. The process according to either claim 1, wherein the concentration of nitro and nitroso compounds is set in the range from 1 to 200 ppm.

4. The process according to claim 1, wherein the process control or regulation of the hydrogenation comprises alteration of the introduction of catalyst and/or nitroaromatics.

5. The process according to claim 1, wherein the aromatic amines are anilines, toluidines, naphthyldiamines, xylylenediamines or toluenediamines.

6. The process according to claim 1, wherein toluenediamine is prepared by hydrogenation of dinitrotoluene and the area of the peaks of dinitrotoluene and aminonitrotoluene in the chromatogram of the reaction mixture is determined to determine the concentration.

7. The process according to claim 6, wherein the dinitrotoluene concentration in the liquid product output from the reactor is set to a value in the range from 1 to 100 ppm by weight, based on the total weight of the liquid product output from the reactor.

8. The process according to claim 1, wherein the hydrogenation is carried out in the presence of nickel-comprising catalysts.

9. The process according to claim 1, wherein the sample of the reaction mixture is maintained at a temperature of at least 80° C. from sampling to analysis or is diluted with a solvent after sampling.

10. A process for preparing aromatic amines by hydrogenation of nitroaromatics in the presence of catalysts, forming a fluid, amine-comprising reaction mixture in a reactor, wherein chromatographic analysis of the reaction mixture or a measurement of the absorption of IR- and/or VIS-radiation through the reaction mixture is carried out to determine the concentration of nitro and nitroso compounds in the reaction mixture, with the result of the determination of the concentration of nitro and nitroso compounds being used for process control or regulation of the hydrogenation, wherein to determine the concentration of the nitro and nitroso compounds, a gas chromatogram of the reaction mixture is produced and evaluated, and wherein the introduction of the reaction mixture into the gas chromatograph is carried out by means of an automated liquid metering valve heated to at least 80° C.

11. The process according to either claim 10, wherein the concentration of nitro and nitroso compounds is set in the range from 1 to 200 ppm.

12. The process according to either claim 10, wherein samples are fed online via a bypass to the chromatograph.

13. The process according to claim 10, wherein the process control or regulation of the hydrogenation comprises alteration of the introduction of catalyst and/or nitroaromatics.

14. The process according to claim 10, wherein the bypass is equipped with an automated liquid metering valve for sampling, optionally with upstream particle filter.

15. The process according to claim 10, wherein the aromatic amines are anilines, toluidines, naphthyldiamines, xylylenediamines or toluenediamines.

16. The process according to claim 10, wherein toluenediamine is prepared by hydrogenation of dinitrotoluene and the area of the peaks of dinitrotoluene and aminonitrotoluene in the chromatogram of the reaction mixture is determined to determine the concentration.

17. The process according to claim 16, wherein the dinitrotoluene concentration in the liquid product output from the reactor is set to a value in the range from 1 to 100 ppm by weight, based on the total weight of the liquid product output from the reactor.

18. The process according to claim 10, wherein the hydrogenation is carried out in the presence of nickel-comprising catalysts.

19. The process according to claim 10, wherein the sample of the reaction mixture is maintained at a temperature of at least 80° C. from sampling to analysis or is diluted with a solvent after sampling.

20. A process for preparing aromatic amines by hydrogenation of nitroaromatics in the presence of catalysts, forming a fluid, amine-comprising reaction mixture in a reactor, wherein chromatographic analysis of the reaction mixture or a measurement of the absorption of IR- and/or VIS-radiation through the reaction mixture is carried out to determine the concentration of nitro and nitroso compounds in the reaction mixture, with the result of the determination of the concentration of nitro and nitroso compounds being used for process control or regulation of the hydrogenation, wherein sampling for the concentration determination is carried out in a bypass for the liquid product output downstream of a product isolation unit or in a bypass for the liquid product output between reactor and product isolation unit and wherein the bypass is equipped with an automated liquid metering valve for sampling, optionally with upstream particle filter.

21. The process according to claim 20, wherein to determine the concentration of the nitro and nitroso compounds, a gas chromatogram of the reaction mixture is produced and evaluated.

22. The process according to either claim 20, wherein the concentration of nitro and nitroso compounds is set in the range from 1 to 200 ppm.

23. The process according to either claim 20, wherein samples are fed online via a bypass to the chromatograph.

24. The process according to claim 20, wherein the process control or regulation of the hydrogenation comprises alteration of the introduction of catalyst and/or nitroaromatics.

25. The process according to claim 20, wherein the aromatic amines are anilines, toluidines, naphthyldiamines, xylylenediamines or toluenediamines.

26. The process according to claim 20, wherein toluenediamine is prepared by hydrogenation of dinitrotoluene and the area of the peaks of dinitrotoluene and aminonitrotoluene in the chromatogram of the reaction mixture is determined to determine the concentration.

27. The process according to claim 26, wherein the dinitrotoluene concentration in the liquid product output from the reactor is set to a value in the range from 1 to 100 ppm by weight, based on the total weight of the liquid product output from the reactor.

28. The process according to claim 20, wherein the hydrogenation is carried out in the presence of nickel-comprising catalysts.

29. The process according to claim 20, wherein the introduction of the reaction mixture into the gas chromatograph is carried out by means of an automated liquid metering valve heated to at least 80° C.

30. The process according to claim 20, wherein the sample of the reaction mixture is maintained at a temperature of at least 80° C. from sampling to analysis or is diluted with a solvent after sampling.

\* \* \* \* \*